US005677331A

United States Patent [19]
Zhou et al.

[11] Patent Number: 5,677,331
[45] Date of Patent: Oct. 14, 1997

[54] ANTIMALARIAL COMPOSITIONS

[75] Inventors: Yiqing Zhou; Dianxi Ning; Shufen Wang; Deben Ding; Guofu Li; Chengqi Shan; Guangyu Liu, all of Beijing, China

[73] Assignees: Ciba-Geigy AG, Basel, Switzerland; Institute of Microbiology and Epidemiology, Academy of Military Medical Sciences, Beijing, China

[21] Appl. No.: 216,440

[22] Filed: Mar. 23, 1994

Related U.S. Application Data

[63] Continuation of Ser. No. 43,998, Apr. 7, 1993, abandoned, which is a continuation of Ser. No. 714,229, Jun. 12, 1991, abandoned.

[30] Foreign Application Priority Data

Aug. 8, 1990 [CN] China ................................ 90106722.9
Apr. 24, 1991 [CN] China ................................ 91102575.8

[51] Int. Cl.⁶ ...................... A61K 31/335; A61K 31/135
[52] U.S. Cl. ........................... 514/450; 514/648; 514/895
[58] Field of Search .................................. 514/450, 648, 514/895

[56] References Cited

FOREIGN PATENT DOCUMENTS 0 362 810  4/1989  European Pat. Off. .

OTHER PUBLICATIONS

Deng, Chemical Abstracts, vol. 112, No. 7, Feb. 12, 1990 p. 1, Abstract No. 48094s.

Deng, Chinese Journal of Pharmaceuticals 1989, vol. 20, No. 8 pp. 372–376.

Who, "Practical Chemotherapy of Malaria", World Health Organization Technical Report Series 805 (1990).

Deng et al., Chemical Abstracts, vol. 114 p. 595 (1991), Abstract No. 6046p.

Wang et al., Chemical Abstracts, vol. 101, p. 385 (1984), Abstract No. 136941u.

CA 97(4): 28538h, Wang et al., 1982.

CA 113(5): 34389a, Sethi et al., 1988.

Merck Index, Therapeutic Catagory p. 16, 1989.

CA 103:134524, Lin et al., 1985.

Primary Examiner—Kimberly Jordan
Attorney, Agent, or Firm—Wenderoth, Lind & Ponack

[57] ABSTRACT

The invention relates to a synergistic antimalarial composition which comprises the antimalarial agent benflumetol and also an antimalarial agent from the artemisinine group such as artemether. The composition can be formulated into solid dosage forms such as tablets and is useful for the treatment of drug resistant malaria.

5 Claims, No Drawings

ANTIMALARIAL COMPOSITIONS

This application is a continuation of now abandoned application Ser. No. 08/043,998, filed Apr. 7, 1993, which is a continuation of now abandoned application Ser. No. 07/714,229, filed Jun. 12, 1991.

The present invention relates to a synergistic antimalarial composition, methods of treating malaria by administering that composition, and to a process for the preparation of that synergistic antimalarial composition.

Drug resistant malaria is a serious clinical and public health problem. The malaria parasite *Plasmodium falciparum* has developed the versatility of evading the effects of standard drugs such as chloroquine either by genetic mutation or by non-genetic adaption methods. The spread of *Plasmodium falciparum* resistant to chloroquine and other antimalarial drugs is a major challenge to health care programms in tropical and subtropical countries. Therefore, novel pharmaceutical compositions which diminish the resistance of malarial parasites, are needed for successful therapy.

The antimalarial effect of compositions containing the individual agent benflumetol has been reported in Chemical Abstracts 97:28538 h and 101:136941u. Other compositions contain combinations of known antimalarial agents. For example, the combination of amodiaquine and tetracycline have been used in the clinic [Suphat Noeypatimanond, et al. (1983), Treatment of *Plasmodium falciparum* malaria with a combination of amodiaquine and tetracycline in central Thailand, Trans. R. Soc. Trop. Med. and Hyg. 73 (3), 338–340]. Recently another antimalarial combination FANSIMED (mefloquine, pyrimethamine and sulphadoxine) is undergoing clinical trials [Tropical Diseases Research, Seventh Programme Report, Chapter 2; Malaria, UNDP World Bank/WHO. Published by WHO, 1985].

The use of combinations of artemisinine, its derivatives and other antimalarial compounds, such as quinine, has been proposed in the Indian Patent Application 26 BOM87 and the German Patent Application P 37 15 378. Also the synergistic effect of a combination of artemisinine and primaquine is known (Wan Yaode, Cang Qizhong, Pharmacy Bulletin, Vol. 16, No. 1, 1981).

Combinations of the antimalarial agents artemether, arteether, artemisinine, dihydroartemisinine, or artesunate with quinidine or with mefloquine have been disclosed in the European Patent Application 362 810.

Motivation for the present invention has been drawn from the need in therapy for an improved antimalarial composition of higher activity and lower resistance against malarial parasites such as *Plasmodium falciparum*.

It has now been found that pharmaceutical compositions containing the active agent benflumetol in combination with the agent artemisinine or especially one of its derivatives such as artemether have excellent antimalarial activity and are more active than compositions containing only the individual component benflumetol, or alternatively, artemisinine derivatives.

The following invention relates to a pharmaceutical composition suitable for synergistic action of the active components against malaria comprising a synergistically effective amount of a compound of the formula:

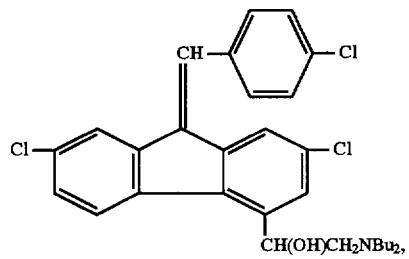

combined with a synergistically effective amount of at least one compound of the formula:

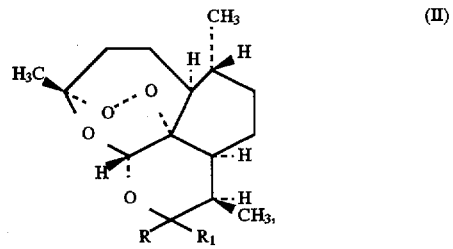

wherein R and $R_1$ together represent oxygen or one of R and $R_1$ individually represents hydroxy, $C_1$–$C_6$-alkoxy, $C_1$–$C_6$-alkenyloxy, $C_1$–$C_5$-alkanoyloxy, carboxy-$C_1$–$C_6$-alkanoyloxy, cyclohexanecarbonyloxy, benzoyloxy or naphthoyloxy and the other represents hydrogen, or a pharmaceutically acceptable salt thereof and optionally pharmaceutically acceptable additives.

The general definitions and terms used in this specification of the invention preferably have the following meanings:

The term pharmaceutical composition defines a mixture comprising the compound of the formula I and at least one compound of the formula II. This mixture either consists of a dry preparation of the active components (I) and (II) such as a lyophilisate or preferably contains additives suitable for the manufacture of a dosage form such as tablets, capsules or suppositories.

The term synergistic action defines the increase of efficacy of the composition above the efficacy level of at least one individual active component at the given dose. Preferably, the efficacy of all active components present in the pharmaceutical composition is increased. The synergistic effect is most desirable as it enables the use of a lower dosage of an individual component and/or improvement of activity above the activity levels of the individual components.

The synergism of the claimed composition is proved by experimental results from in-vitro and in-vivo models. The results show that the activity of the component according to formula I is raised as compared to the activity of benflumetol (I) in an individual dosage form and that the activity of the component (II) such as artemether is also being raised.

Synergistic action against malaria of the composition according to the present invention permits the combined application of different drug regimens during therapy by the administration of one dosage form such as one or two tablets per day.

The application of a dosage form comprising the active component benflumetol (I) allows permanent action against malaria. The presence of the second active component (II) in the same dosage form such as artemether (one of R and $R_1$ represents hydrogen and the other represents methoxy) allows immediate and fast action against protozoa after the outbreak of the disease. This is evident from tests carried out in different standard in-vitro and in-vivo pharmacological models.

The active component (I), wherein Bu denotes n-butyl, is known under the name benflumetol, see C.A.R.N. 82186-77-4. Pharmaceutical compositions containing benflumetol individually and its activity against malaria are also known, see the abstracts according to C.A. 97:28538h and 101:136941. The preparation of benflumetol has been disclosed in the Published Chinese Patent Application 88/07666.X.

The active component (II) wherein R and $R_1$ together represent oxygen is known under the name artemisinine. The component (II) wherein one of R and $R_1$ represents hydrogen and the other represents hydroxy is named dihydroartemisinine.

In a compound of the formula II $C_1$–$C_6$-alkoxy preferably represents methoxy or ethoxy. The compound (II) wherein one of R and $R_1$ represents methoxy and the other represents hydrogen is known under the name artemether. The compound (II) wherein one of R and $R_1$ represents ethoxy and the other also represents hydrogen is known under the name arteether.

In a compound of the formula II $C_1$–$C_6$-alkenyloxy is preferably allyloxy. $C_1$–$C_5$-alkanoyloxy is preferably acetoxy or propionyloxy. Carboxy-$C_1$–$C_6$-alkanoyloxy is preferably carboxy-n-propionyloxy. The carboxy group may be present in salt form (carboxylate), e.g. as sodium or potassium salt. The compound (II) wherein one of R and $R_1$ represents sodium carboxylate-n-propionyloxy (—O—CO—$CH_2$—$CH_2$—$CO_2$—Na) and the other represents hydrogen is named artesunate.

The active components artemisinine, dihydroartemisinine, arteether and artesunate comprised by formula II are preferred. Especially preferred is artemether.

The generic names used in the specification of the present invention are taken from "Tropical Diseases Research, Seventh Programme Report", Chapter 2; Malaria, UNDP WORLD BANK/WHO, Published by WHO, 1985.

The active components (II) artemisinine, dihydroartemisinine, arteether, artemether and artesunate are known. Artemisinine has been isolated from *Artemisia annua* L. and subsequently synthesized. It has been used for the treatment of Falciparum malaria [H. P. Koch (1981) Qinghasosu: a potent antimalarial from plant origin, Pharmacy International (New Drugs), p. 184–185, Elsevier North Holland Biomedical Press; L. J. Bruce-Schwatt (1982), Qinghaosu: a new antimalarial, British Med. J., 184, 767–768]. The clinical evaluation of the activity of artemisinine in 2069 patients was reported by Koch in 1981, of which 1511 patients were treated for a vivax malaria [H. P. Koch (1981) Qinghaosu: a potent antimalarial from plant origin, Pharmacy International (New Drugs), p. 184–185, Elsevier North Holland Biomedical Press]. It has also been shown to be active against chloroquine-resistant strains of *Plasmodium falciparum* in man [J. P. Jiang et al. (1982), Antimalarial activity of mefloquine and qinghasosu. Lancet, ii. 8293, 185–287]. Dihydroartemisinine, arteether, artemether, artesunate are semi-synthetic derivatives of artemisinine. Their antimalarial activity is disclosed in different WHO reports. [WHO. Report of the Scientific Working Group on the Chemotherapy Malaria, TDR/Chemal 3rd Review, 85. 3, Geneva, 3–5. Jun. 1985 and the references contained therein].

Conventional pharmaceutically acceptable additives are preferably present in the composition according to the present invention. The additives are used for the preparation of enteral or parenteral dosage forms according to conventional formulation methods.

For oral administration suitable additives include inert diluents or fillers, thereby forming dosage forms such as tablets, powders, capsules, and the like. The pharmaceutical compositions can, if desired, contain additional ingredients such as flavourings, binders, excipients and the like.

For example, tablets containing various solid additives such as starch, dextrin, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard gelatin capsules, preferred materials therefore include lactose or milk sugar and high molecular weight polyethylene glycols.

For other oral dosage forms the mixture of the compounds can for example be administered in a gelatin capsule. Such formulation could be based on a suitable refined edible oil such as sunflower oil, corn oil, peanut oil, coconut oil or til oil.

In a preferred embodiment of the present invention, the active components (I) and (II) are formulated in a single unit dosage form such as tablets or capsules.

The active components (I) and (II) may also be formulated into two individual dosage forms contained within one administration system (kit of parts), which are simultaneously or consecutively administered. The same route of administration is possible, e.g. administration of two individual dosage forms contained within one kit of parts. One tablet or capsule containing component (I) and, consecutively, a second dosage form containing component (II) is administered. An individual dose regimen may be developed especially during clinical treatment, e.g. by administering after the first occurrence of malaria a tablet or capsule containing a high dose of the active component (II) or, correspondingly, multiplying lower doses in the beginning of malaria attacks, and administering also a tablet or capsule containing a lower dose of the active component (I). In the course of treatment, dosage forms containing a lower dose of component (II) are administered. Different dosage forms present in one kit-of-parts may also be administered simultaneously or consecutively, e.g. by administration of a tablet containing component (I) and a suppository containing component (II). The dosage range may also be varied according to the dose regimens given above.

The usefulness of the pharmaceutical composition according to the present invention in therapy against malaria is evident from in-vitro and in-vivo results from experiments carried out in established test models. Some results are given in the Examples. The ability of the composition to act as an effective and rapid acting antimalarial agent even against strains of *P. berghei* known to be extremely resistant against other antimalarial agents reflects the usefulness of the present invention.

The present invention also relates to a method of treatment against malaria which comprises administering to a patient after the outbreak of malaria the above-mentioned pharmaceutical composition comprising the combined active components (I) and (II). The composition is administered to the patient for a period of time of at least four days, preferably five or more days.

The term method of treatment also comprises prophylactic administration of the composition to healthy patients to prevent the outbreak of the disease in high-risk areas of contamination, especially in regions between the tropics of capricorn and cancer.

The dose of the active component benflumetol (I) as contained in the pharmaceutical composition may vary within wide limits and depends on the condition of the patient and the time period elapsed after the outbreak of the disease. Based on in-vivo data from *P. berghei* model experiments with mice as reported below in the Examples, it is established that the daily dose of benflumetol is between about 0.2–5.0 mg/kg, preferably 0.2–10.0 mg/kg and especially about 0.2–5.0 mg/kg. This daily dose can be raised considerably upon need in view of the low toxicity and high tolerability of benflumetol. It is also estimated that the daily dose of component (II) in the composition, especially artemether, is between 0.2 and 5 mg/kg, preferably 0.3–3.0 mg/kg and especially between about 0.4–5.0 mg/kg.

The dose ratio of component (I) to component (II) may also vary within wide limits. It has been determined that synergism will be especially efficient if benflumetol is administered in equal weight amounts or, preferably, in excess amounts as compared to the weight amounts of component (II) administered. Accordingly, the weight amount of benflumetol may vary from one to ten parts for each part of component (II), especially artemether administered. Preferably, three to seven parts and especially five to six parts of benflumetol are administered for each part of component (II). The dose amounts given and dose ratios refer to daily administrations.

The invention also relates to a process for the preparation of the pharmaceutical composition suitable for synergistic action of the active components against malaria which comprises combining an effective amount of a compound of formula I with an effective amount of a compound of the formula II and formulating this combination of active components under optional addition of pharmaceutically acceptable additives to a suitable dosage form.

The novel pharmaceutical compositions contain, for example, from 10% to 80%, preferably from 20% to 60%, of the combination of active components. Pharmaceutical compositions according to the invention are suitable for enteral administration and are, for example, formulated into oral dosage unit forms, such as dragées, tablets, capsules or suppositories. These are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary, after the addition of suitable adjuncts, to form tablets or dragée cores.

In a preferred embodiment of the process, the active components (I) and (II) are milled either individually or together to particle sizes from about 10µ to about 400µ, preferably 20µ to 200µ. At least 90% of the crystals of the active components are present in these ranges.

Particles of this size are obtained by conventional comminution methods, e.g. grinding in an air jet mill, ball mill or vibrator mill. Micronisation is preferably effected by per se by known methods using an ultrasonics disintegrator, e.g. of the Branson Sonifier type as described e.g. in J. Pharm. Sci. 53 (9), 1040–1045 (1965), or by stirring a suspension with a high-speed agitator, for example with a stirrer of the Homorex type (supplied by Brogli & Co., Basel). In these preferred methods, micronisation is effected at about 500 to 10,000 rpm by dissolving or suspending the combination of active components in an organic solvent, e.g. methanol, ethanol or propylene glycol, and precipitating it in microcrystalline form at ca. 0°–5° C. in water or an aqueous salt solution, e.g. 2% sodium chloride solution which may additionally contain a protective colloid such as gelatin or a cellulose ether, e.g. methyl cellulose or hydroxypropyl methyl cellulose, in low concentration (0.1–1%), and filtering the resultant stirred suspension. The filter cake is dried at low temperature, e.g. ca. 0°–5° C., under vacuum (e.g. below 50 mbar, preferably at 0.5 mbar). The subsequent drying can be effected at ca. 50°–90° C.

The crystals thus obtained are then formulated to granulates, preferably by wet granulation which is carried out according to standard methods.

The pharmaceutical composition is preferably prepared by compressing a granular formulation which is obtained, for example, by sieving and, if desired, by comminuting the drug, with or without the excipients, compacting with another solvent such as ethanol or water, removing the solvent or drying, with or without the addition of lubricants or glidants such as magnesium stearate or TWEEN, comminuting the granules and sieving once more.

The granules can be compressed to tablet cores in a conventional tabletting machine, for example an EKO Korsch eccentric tabletting machine, at a pressure of ca. 10 kN. Coating can be effected by applying an aqueous-ethanolic solution in which, for example, polyethylene glycol and saccharose is dissolved or dispersed.

Dragée cores are provided with suitable coatings that may be resistant to gastric juices, there being used, inter alia, concentrated sugar solutions that may contain gum arabic, talc, polyvinylpyrrolidone or polyethylene glycol. Colorings or pigments may be added to the tablets or dragée coatings, for example for identification purposes or to indicate different doses of the active ingredient.

Further orally administrable pharmaceutical compositions are dry-filled capsules consisting of gelatin, and also soft sealed capsules consisting of gelatin and plasticiser, such as glycerine or sorbitol. The dry-filled capsules may contain the active components in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

Suitable for enteral administration are also suppositories that consist of a combination of the active ingredient and a suppository base. Suitable as suppository bases are, for example, natural or synthetic triglycerides, paraffins, polyethylene glycols or higher alkanols. It is also possible to use gelatin rectal capsules that contain a combination of the active ingredient and a base material; suitable base materials are, for example, liquid triglycerides, polyethylene glycols or paraffin hydrocarbons.

The following Examples illustrate the invention described above; they are not, however, intended to limit the scope of the invention in any way.

EXAMPLE 1

Determination of dose ratios for the combination of benflumetol with artemether:

Albino mice were infected with *Plasmodium berghei* as test strain. By using orthogonal design, parallel contrast experiments were carried out for different doses of the combination according to the "4-day inhibition test" method. $ED_{50}$ or $ED_{90}$ and the synergistic indices were calculated by means of a linear regression equation.

$$\text{Index of synergism} = \frac{ED_{50} \text{ or } ED_{90} \text{ for individual component}}{ED_{50} \text{ or } ED_{90} \text{ for that component in combination}}$$

Using this equation, the optimal weight ratio of drugs in this combination against murine malaria is calculated to be 2:0.75 (the index synergism for ED90>6). Based on experiments in murine malaria, experiments in rhesus monkey with *Plasmodium Knowlesi* were performed and the result showed that the optimal weight ratio of drugs in this combination against malaria is 3–6 parts of benflumetol to each part of artemether.

EXAMPLE 2

The synergism between the components benflumetol and artemether is determined according to the method of Peters: Am. Trop. Med. Parasitol Vol. 62, pg. 488–492 (1968). The results are reported in the following Table:

Blood schizintocidal action of artemether (A) and benflumetol (B) administered orally in varying proportions to mice infected with *P. Berghei* $K_{173}$ N-strain in "4-day test" according to Peters (Mean values of three experiments)

| Drug and dose (mg/kg/day) | Effective dose of first component (mg/kg/day) | |
|---|---|---|
| | $ED_{50}$ | $ED_{90}$ |
| Benflumetol (B) | 1.30 | 2.70 |
| +A 0.25 | 0.84 | 1.84 |
| +A 0.50 | 0.78 | 1.57 |
| +A 1.00 | 0.51 | 1.16 |
| +A 2.00 | 0.16 | 0.57 |
| +A 4.00 | 0.06 | 0.29 |
| Artemether (A) | 2.00 | 5.30 |
| +B 0.37 | 1.49 | 4.46 |
| +B 0.50 | 0.87 | 2.67 |
| +B 0.75 | 0.93 | 3.44 |
| +B 1.00 | 0.37 | 1.21 |
| +B 1.50 | 0.25 | 0.83 |

All points representing $ED_{50}$ and $ED_{90}$ of the components A and B present in the combination being located beneath the addition indicate synergism between the individual components.

EXAMPLE 3

The rate of killing protozoa was determined in-vivo. When the protozoa concentration in the blood of mice increased to high density, a multiple dose equivalent, i.e. 20× $ED_{90}$ was given intragastrically. The rate of decrease of protozoae in blood was observed uninterruptedly after administration. The timespan required for 90% decrease of the protozoae was 49.7 hours for the combination and 64.3 hours for benflumetol alone. Artemether alone could not kill protozoa by more than 90% before their number increased again.

EXAMPLE 4

Clinical determination of the best ratio of dose combination between artemether and benflumetol in the combination:

Based on the result of animal experiment with reference to the clinical effective doses of artemether and benflumetol singly, the optimal ratio of dose combination of these two components was calculated to be from 1:4 to 1:6. For example when 1:6 is chosen, the doses of artemether and benflumetol in each tablet would be 20 mg and 120 mg respectively. Two groups of patients given the combination with 1:5 and 1:6 ratios were selected for clinical parallel comparison trials. In both groups, the "3 days and 4 doses" treatment scheme was adopted, i.e. 4 tablets were administered at the first time and then 4 tablets each for three more times with 8, 24 and 48 hour intervals. That made altogether 16 tablets for each adult. 40 cases of pernicious malaria were selected and divided randomly into two groups. The following parameters were determined in these two groups after administration: 1) rate for decrease of protozoae at 24 hours; 2) average time for disappearance of protozoae; 3) average time for subsidence of fever; 4) 28-day cure rate.

The results showed that at 24 hours after administration the rates of decrease in protozoa in these two groups were 96.3% and 94,2%, the time periods for disappearance of protozoae were 34.8 hours and 36.0 hours and the average time periods for subsidence of fever were 23.2 hours and 22.4 hours respectively. However, the recrudescence rate on the 281th day in the 1:5 group was 20% as compared to 0% in the 1:6 group (i.e. all of the patients in this group were cured). These results indicate that the optimum ratio of combination of artemether and benflumetol in the combination for treatment of human malaria is 1:6.

EXAMPLE 5

Toxicological Evaluation of the artemether-benflumetol combination:

The ratio of combination of 1:6 for artemether and benflumetol was used in these experiments. The medium lethal dose (LD50) for albino mice was found in acute toxicity experiments to be 4555 mg/kg for oral administration. Based on grading criteria for chemical toxicity, this complex prescription is of low grade of toxicity. Toxicity experiments for 14 days were performed in rats and beagles, which were divided into high-, medium- and low-dose groups. Drugs were administered per os once every day for successive 14 days. Appetite and body weight were observed, hematological and biological parameters were determined, and pathological examinations were made in major viscera and target organs of the drugs. The results revealed that the basic safety dose in rats was being equivalent from 40-fold to 50-fold of the dose administered to humans. Although some abnormal changes were found in target organs (liver and kidney)in higher dose groups, they recovered to normal on day 28 after administering the last dose. These results indicated that the toxicity of the synergistic combination is low, and the safety range is wide and free from irreversible toxic reactions.

EXAMPLE 6

Determination of therapeutic effect of individual components as compared to synergistic combination:

Two groups of patients were selected for oral administration and the 3 days and 4 doses treatment scheme. There were 20 patients with pernicious malaria in each group. The therapeutic effect of the combination and artemether and benflumetol singly were compared separately. The doses of both drugs in individual administration were about the same as in the complex prescription. The parameters determined were: 1) the rate for decrease of protozoa at 24 h post administrationem; 2) average time for disappearance of protozoae; 3) average time for fever subsidence; and 4) cure rate at the 28th day.

The rates of decrease in protozoae at 24 hours after administration were found to be 97%, 95.1% and 74.5% for the combination, individual artemether, and individual benflumetol respectively. The times for disappearance of protozoae were 35.6 h, 38.7 h and 68.4 h respectively. The average time for fever subsidence was 23.8 h, 19.7 h and 40 h and the 28-day cure rates were 95%, 45% and 65% respectively. This experimental therapeutic scheme indicated clearly the superiority in therapeutic effect of the combination over the individual drugs.

EXAMPLE 7

Additional clinical trials for the combination artemether/benflumetol:

a) With the 3 days and 4 doses schemes and oral administration, altogether 400 patients with pernicious malaria were treated. Main parameters observed were: 1) average time period for disappearance of protozoae (the results were 23.2–41.0); 2) average time period for subsidence of fever (20.4–25.7); 3) 28-day cure rate (average 96.8%).

b) The combination composition was also administered with the 3 days and 4 doses treatment scheme, i.e. 4 tablets the first time and then 4 tablets each time at 8, 24 and 48 h with a total of 16 tablets for adults. 48 vivax malaria patients were treated with the combination. The parameter observed were 1) average time for disappearance of protozoa (the results were 22.8±9.5 h) average time for subsidence of fever (13.6±6.9 h); 3) 28-day cure rate (91.67%). These results demonstrated remarkable therapeutic effect of the combination against vivax malaria.

EXAMPLE 8

Preparation of Tablets.
benflumetol 120 mg
artemether 20 mg
corn starch 100 mg
dextrin 40 mg
Tween®-80 0.6 mg
15% paste of corn starch "sufficient"
Mg-stearate 3 mg Artemether crystals are passed trough a 100 mesh size sieve. Benflumetol crystals are passed through a 60 mesh size sieve and mixed with the artemether solid, starch and dextrin. This mixture is passed 3 times through a 40 mesh size sieve. Tween®-80 is added to the paste of starch which is mixed with the above formulation. This mixture is granulated by way of wet-granulation, passed through a 40 mesh size sieve, dried at reduced pressure at 50°–60° C.. The Mg-stearate is added, and the tablets are pressed.

We claim:

1. A pharmaceutical composition to be administered orally to humans, suitable for synergistic action of the combined active components against malaria, which composition consists of a synergistic antimalarially effective amount of a combination of the compound benflumetol of the formula:

(I)
[structure with CH, Cl substituents on fluorene ring system, CH(OH)CH$_2$NBu$_2$]

in fixed combination with the compound artemether of the formula:

(II)
[structure of artemether with CH$_3$, H$_3$C, O, H, R, R$_1$, CH$_3$ substituents]

wherein one of R and R$_1$ individually represents methoxy, and the other represents hydrogen,
and pharmaceutically acceptable additives.

2. A pharmaceutical composition according to claim 1, which composition consists of a synergistically effective amount of one to ten parts by weight of benflumetol (I) for each part by weight of artemether (II).

3. A pharmaceutical composition according to claim 1, which composition consists of a synergistically effective amount of three to seven parts by weight of benflumetol (I) for each part by weight of artemether (II).

4. A pharmaceutical composition according to claim 1 which composition consists of a synergistically effective amount of five to six parts by weight of benflumetol (I) for each part by weight of artemether (II).

5. A method of treating malaria which comprises administering orally to a human in need of such treatment a synergistic antimalarially effective amount of a combination of benflumetol of formula (I) and artemether of formula (II).

* * * * *